United States Patent [19]

Wada et al.

[11] Patent Number: 4,679,563
[45] Date of Patent: Jul. 14, 1987

[54] BIOMEDICAL ELECTRODE

[75] Inventors: Shintaro Wada; Hisanori Takahashi; Yoichi Nomura, all of Osaka, Japan

[73] Assignee: Nitto Electric Industrial Co., Ltd., Japan

[21] Appl. No.: 823,175

[22] Filed: Jan. 28, 1986

Related U.S. Application Data

[63] Continuation-in-part of Ser. No. 761,723, Aug. 2, 1985.

[30] Foreign Application Priority Data

Oct. 8, 1984 [JP] Japan .............................. 59-152182[U]
Oct. 8, 1984 [JP] Japan .............................. 59-152183[U]
Dec. 27, 1984 [JP] Japan .............................. 59-201623[U]
Dec. 27, 1984 [JP] Japan .............................. 59-201624[U]

[51] Int. Cl.4 ................................................ A61B 5/04
[52] U.S. Cl. ..................................... 128/640; 128/798
[58] Field of Search ................ 128/639, 640, 731, 798

[56] References Cited

U.S. PATENT DOCUMENTS 4,524,087 6/1985 Engel .................................. 128/639
4,554,924 11/1985 Engel .................................. 128/640

FOREIGN PATENT DOCUMENTS

WO81/01646 6/1981 PCT Int'l Appl. ................. 128/640

Primary Examiner—Kyle L. Howell
Assistant Examiner—Randy Citrin
Attorney, Agent, or Firm—Sughrue, Mion, Zinn, Macpeak & Seas

[57] ABSTRACT

A biomedical electrode comprising a flexible electrode plate which conforms to the skin surface of a living body, and an electrically conductive adhesive layer which fixes the electrode plate on the skin surface and transmits an electric signal from the living body to said electrode plate, wherein a non-contact area to which said conductive adhesive layer is not substantially bonded is formed on the electrode plate and an electrically conductive tongue for connecting a terminal which takes said electric signal from the living body to a biomedical diagnostic apparatus is provided on the non-contact area by forming cut thereon.

9 Claims, 14 Drawing Figures

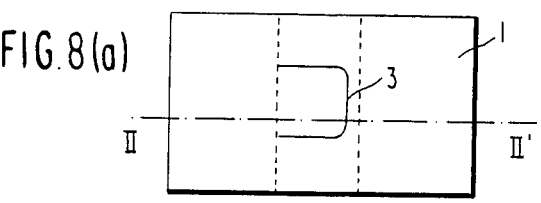
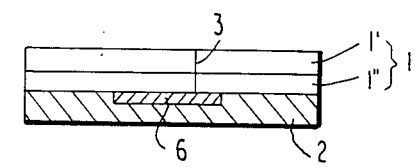
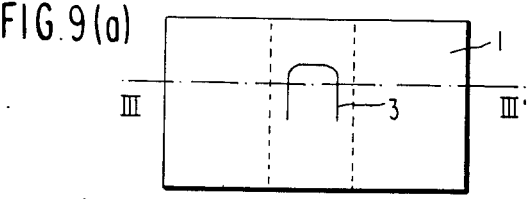
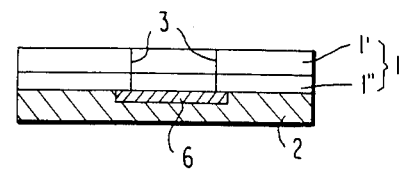
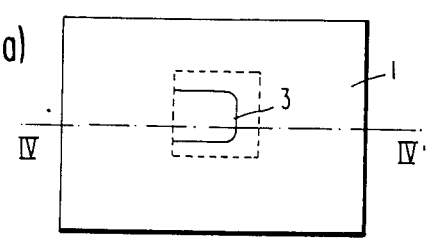
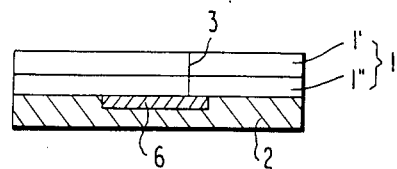

BIOMEDICAL ELECTRODE

CROSS REFERENCE TO THE RELATED APPLICATION

This application is a continuation-in-part application of Ser. No. 761,723 filed on Aug. 2, 1985, entitled "BIOMEDICAL ELECTRODE", now pending.

FIELD OF THE INVENTION

The present invention relates to a biomedical electrode for taking out or receiving an electric signal generated from a living body.

The term "biomedical electrode" as used hereinafter means an electrode for establishing an electrical connection between the skin of a living body and an electromedical apparatus.

BACKGROUND OF THE INVENTION

Various electrodes which are adhered and secured to the skin surface of a patient have been developed as a biomedical electrode to a cardiomotile electric current and potential. In such electrodes, an electrically conductive cream or paste is interposed between the electrode and the skin surface of the living body to improve electrical contact.

On the other hand, a substantially circular disposable biomedical electrode has been developed from the standpoint of the convenience of its application to the skin. This biomedical electrode comprises an electrically conductive electrode plate of metal foil having provided on one side thereof an electrically conductive adhesive layer. This conventional disposable biomedical electrode is designed to have a tab on the edges of the electrically conductive plate so as to connect it to a biomedical diagnostic apparatus. This conventional biomedical electrode is advantageous in its attachment to a body and handling, and also unnecessity of cleaning up the skin surface as compared with use of the electrically conductive cream or paste.

The use of the electrically conductive cream or paste involves various disadvantages in complication of its application, poor adhesion to the skin when sweated, and contamination of the skin surface.

Further, the conventional biomedical electrode is arranged to have the tab on the edges of the electrically conductive electrode plate, so that when a lead wire terminal such as a clip or the like which connects to the biomedical diagnostic apparatus is coupled to the tab, stress is exerted. Such stress is also applied to the marginal edge of the electrically conductive adhesive layer to lift the biomedical electrode by means of the terminal, thereby involving cleavage stress between the skin surface and the adhesive layer after connection. For this reason, the conductive adhesive layer is lifted beyond the tab or peeled therefrom to result in lack of stability of electric signal due to poor adhesion. This is also the prominent phenomenon when the biomedical electrode is used in monitoring for a long period of time.

The electrically conductive electrode plate comprises silver/silver chloride, nickel, tin, chromium or the like, which is a non-polarizable material and an expensive material. Considering reduction in production cost which is an important factor as a ready and disposable biomedical electrode, a formation of the tab which extends beyond the edges of the electrode plate is not considered to be satisfactory from the standpoints of complication of production step and the decrease of yield.

SUMMARY OF THE INVENTION

The present invention is provided to overcome the above-described problems.

An object of the present invention is to provide a biomedical electrode having a structure such that an electrode tongue which is formed by providing cut in the inside region of an electrode plate is capable of connecting a lead wire terminal for connecting a biomedical diagnostic apparatus without deteriorating adhesion, is capable of using it as a monitoring electrode for a long period of time in a stable manner and is capable of manufacturing at a low cost.

The biomedical electrode according to the present inevention comprises a flexible electrode plate which conforms to the skin surface of a living body and an electrically conductive adhesive layer which fixes the electrode plate on the skin surface and transmits an electrical signal from the living body to the electrode plate, wherein a non-contact area to which the conductive adhesive layer is not substantially bonded is formed on the electrode plate and an electrically conductive tongue for connecting with a terminal which takes the electric signal from the living body to a biomedical diagnostic apparatus is provided on the non-contact area by forming cut thereon.

BRIEF DESCRIPTION OF THE DRAWINGS

FIG. 1 (b) is a sectional view taken along the line I—I' of the biomedioal electrode shown in FIG. 1;

FIGS. 8 (a), 9 (a) and 10 (a) each is a plan view of the biomedical electrode according to the present invention; and FIGS. 8 (b), 9 (b) and 10 (b) each is a sectional view taken along the lines II—II', III—III' and IV—IV' of the biomedical electrodes shown in FIGS. 8 (a), 9 (a) and 10 (a), respectively.

DETAILED DESCRIPTION OF THE INVENTION

A biomedical electrode according to the present invention will be explained in detail by reference to the accompanying drawings.

Figure 1A:
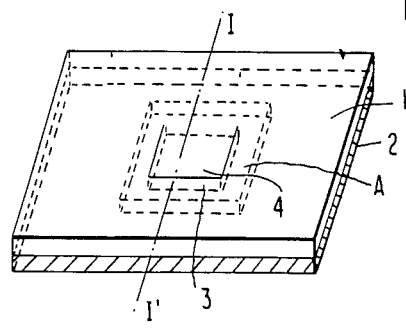
FIG. 1 (a) is a perspective view of a biomedical electrode according to the present invention.
Figure 1B:
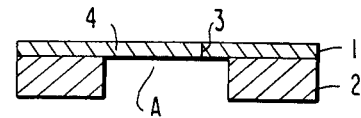

FIG. 1 (a) is a perspective view showing one embodiment of the biomedical electrode according to the present invention, and FIG. 1 (b) is a sectional view taken along the line I—I' of FIG. 1 (a). An electrically conductive adhesive layer is provided on the entire circumferential area of a flexible electrode plate 1 which conforms to the skin surface of a living body. An electrically conductive tongue 4 which can connect to a biomedical diagnostic apparatus is formed by cut 3 in a substantially U-shaped configuration on the electrode plate 1 corresponding to a non-contact area A formed at the center portion of the electrode plate. The electrically conductive tongue 4 formed by the cut 3 is lifted from the portion of cut 3 when the biomedical electrode is used.

Figure 2:
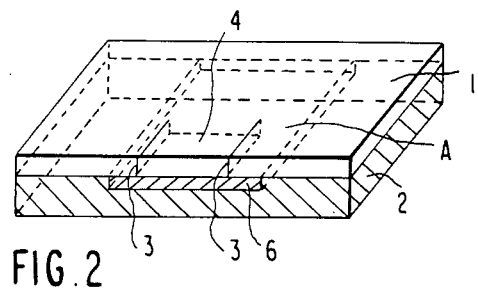
FIG. 2 is a perspective view of another embodiment of the biomedical electrode according to the present invention.

FIG. 2 is a perspective view of another embodiment of the biomedical electrode according to the present invention. A member 6 which is non-tacky to the flexible electrode plate 1 is interpositioned between the center portion of the plate 1 and an electrically conductive adhesive layer 2 and is forming the noncontact area A. The electrically conductive tongue 4 is formed in the inside region of the electrode plate 1 by providing two cuts 3 extending from the one edge of the plate 1 which abuts on the non-tacky member 6.

Figure 3:
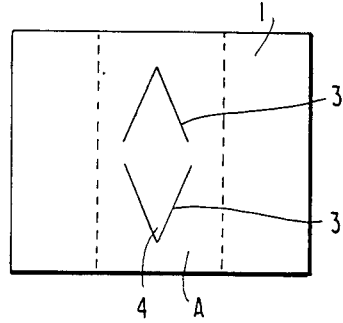
FIG. 3 is a plan view of a further embodiment of the biomedical electrode according to the present invention.

FIG. 3 is a plan view of another embodiment of the biomedical electrode according to the present invention and shows another method for providing cuts 3 to form the electrically conductive tongue 4. V-shaped cuts 3 are provided such that the open side of the V-shape faces each other. The electrically conductive tongues 4 formed by the cuts 3 can be raised to form a two-ply so that a lead wire terminal which is used to transmit the electric signal obtained to the biomedical diagnostic apparatus is firmly connected to the tongues.

Figure 4:
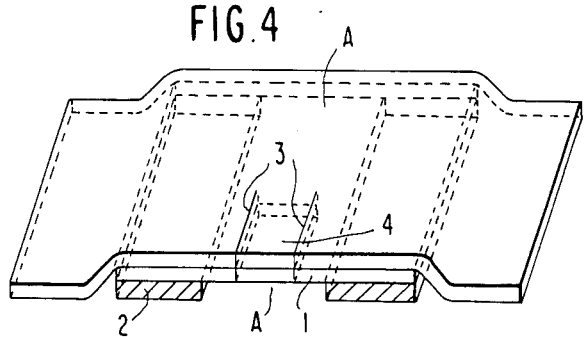
FIGS. 4 and 5 are perspective and plan views, respectively, each showing the biomedical electrode according to the present invention to which the adhesive sheet is adhered.
Figure 5:
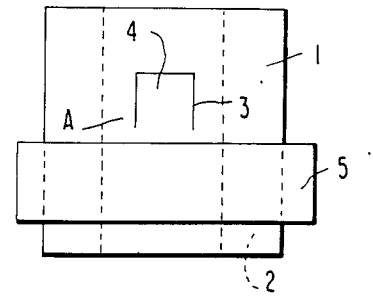

FIGS. 4 and 5 are perspective and plan views showing other embodiments of the biomedical electrode according to the present invention, respectively. An adhesive, preferably a pressure adhesive, sheet 5 is applied to the electrode plate 1 to ensure fixation of the biomedical electrode to the skin surface. In FIG. 4, the adhesive sheet 5 is applied to the entire surface of the one side of the electrode plate 1 so as to extend at least two facing ends thereof and the cuts 3 are formed so as to pass the electrode plate 1 and the adhesive sheet 5 therethrough to form the electrically conductive tongue 4. In FIG. 5, the adhesive sheet 5 is applied to the electrode plate 1 so as to extend the two facing ends of the plates. In this manner, the adhesive sheet 5 is applied to the electrode plate 1 so as to come close to the ends of the cut 3 so that the adhesive layer 2 can be prevented from being peeled from the skin surface or so that the ends of cuts 3 can be prevented from being split by tearing stress generated when the conductive tongue 4 is made upright, thereby ensuring a sufficient adhesion and fixation of the sheet to the skin surface.

Figure 6:
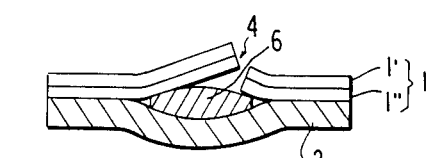
FIGS. 6 and 7 are sectional view of the biomedical electrode according to the present invention, each incorporating the non-tacky member therein.

FIG. 6 is a sectional view showing further embodiment of the biomedical electrode according to the present invention. The non-contact area which is not substantially adhered is constituted by placing thereon an elastomer such as a foamed article in a compressed state. The electrically conductive tongue 4 is readily raised and lifted away from the electrode plate 1 having the cut 3 by the rebound stress of the elastomer by using the elastomer as the non-tacky member 6, thereby facilitating the connection of the lead wire terminal.

Figure 7:
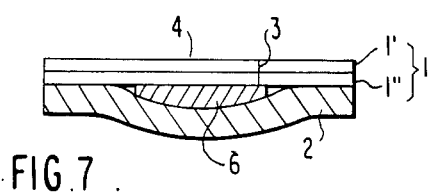

FIG. 7 is a sectional view showing a still further embodiment of the biomedical electrode according to the present invention. The non-tacky member 6 is formed on a thick non-elastomer instead of the elastomer as shown in FIG. 6. The electrically conductive adhesive layer 2 corresponding to the portion of the member 6 is projected to the skin contact side so that the member 6 serves to rise the tongue 4 upright when the biomedical electrode is applied to the skin.

FIGS. 8 (a), 9 (a) and 10 (a) each is a plan view showing still another embodiment of the biomedical electrode according to the present invention, and FIGS. 8 (b), 9 (b) and 10 (b) are sectional views taken along the lines II—II', III—III' and IV—IV' of the biomedical electrodes shown in FIGS. 8 (a), 9 (a) and 10 (a), respectively. Cut 3 is formed in a substantially U-shaped configuration on the electrically insulating layer corresponding to the area of a non-tacky thin layer 6. The cut 3 may be formed on the area beyond the non-tacky layer region, but is preferably formed within the non-tacky layer region. The non-tacky thin layer 6 is embedded in the electrically conductive adhesive layer 2.

The electrode plate 1 functions as a medium for transmitting the electric signal taken out of the skin surface through the adhesive layer 2 to the biomedical diagnostic apparatus. Examples of the plate 1 are sheet-like material of a metal such as copper, tin, nickel, aluminum or silver; and a sheet-like material having an electroconductivity such as a plastic film, a paper, a woven fabric or a nonwoven fabric, each having a metallic thin layer provided thereon by electroless plating, vacuum deposition or laminating means. The electrode plate is used by appropriately selecting material having a flexibility sufficient to conform to the skin to which the plate is applied.

As shown in FIGS. 6 to 10, an electrically insulating layer 1' is laminated to a conductive layer 1" on the side opposite to the electrically conductive layer 2, thereby preventing noises derived from the contact when the biomedical electrode is applied to the skin and the electric signal is taken out therefrom.

The electrically insulating layer 1' is not limited to a single layer, but can be a laminate comprising at least two layers. Examples of the material for the electrically insulating layer are various synthetic resins such as polyethylene terephthalate, polyester and the like, and foamed materials such as polybutadiene foam, polyethylene foam, ethylene-vinyl acetate foam and the like.

Examples of the laminate for the electrically conductive layer are a laminate comprising a polyethylene terephthalate film and a film selected from a polybutadiene foam, a polyethylene foam and an ethylene-vinyl acetate foam; and a laminate comprising a polyester film and a film selected from a polybutadiene foam, a polyethylene foam and an ethylene-vinyl acetate foam.

If desired, functional materials such as woven fabrics, nonwoven fabrics, net-like materials, foamed articles or synthetic films can be provided on the electrically insulating layer 1' according to the purpose. This is particularly effective to prevent the ends of the cut formed on the electrode plate 1 from tearing.

The electrically conductive adhesive layer 2 disposed on the electrode plate 1 is a flexible layer (including gel) for transmitting the electric signal received from the skin to which the biomedical electrode is applied to the biomedical diagnostic apparatus. The adhesive layer 2 is formed of a material having an electroconductivity. Materials for the adhesive layer are polysaccharide such as Karaya gum; semisynthetic high polymer such as various cellulose; and a synthetic high polymer such as polyacrylic acid (or its salt), polyacrylic ester derivative, homopolymer or copolymer of polyvinyl alcohol or other hydrophilic polymer. For the purpose of further improving the electroconductivity of high polymer, electrically conductive materials such as various metal powders, carbon, water and electrolyte such as KCl or NaCl can be added thereto. Further, the electrically conductive material can be used in combination with conventional materials having no electroconductivity.

Although the electrically conductive adhesive layer 2 composed of the high polymer can be applied on the electrode plate 1 directly, a reinforcing sheet which does not inhibit the electroconductivity of the layer 2 can be interpositioned between the plate 1 and the layer 2 to improve a shape retention property thereof and avoid contamination such as an adhesive residue on the skin. Further, from the practical standpoint, it is preferred that the reinforcing sheet is present (embedded) in the layer 2. Examples of these reinforcing sheet are paper, woven or nonwoven fabric, various plastic films and meshes, and metal foil. The reinforcing sheet can be also used by providing through holes if it lacks the electroconductivity.

According to the present invention, the non-contact area A to which the adhesive layer 2 is not substantially bonded can be formed by providing non-formation area of the electrically conductive adhesive layer 2 on the electrode plate 1. However, the non-contact area A can also be formed by disposing a substantially non-tacky member 6 on the electrode plate 1 as shown in FIGS. 2 and 6 to 10. The non-tacky member 6 is a layer as shown in FIGS. 2 and 8 to 10 to facilitate raising of the electrically conductive tongue 4 formed in the electrode plate 1. The member 6 is non-tacky or difficult to adhere to the electrically conductive tongue 4. Examples of the member 6 are a layer selected from various plastic films, a woven or nonwoven fabric, papers and metals. The member 6 is also obtained by applying a low adhesive material such as silicone or fluorine. As shown in FIG. 6, by using a thick elastomer having a thickness of 0.5 mm to ten-odd mm as the non-tacky member 6, the compressive stress caused when the member 6 is interposed between the electrode plate 1 and the adhesive layer 2 is released by the cut and the tongue 4 is automatically raised by the rebound stress to facilitate connection of the lead wire terminal. Further, by simply using a thick non-tacky member as the non-tacky member 6 as shown in FIG. 7, the electrically conductive tongue 4 can be made upright through the cut 3 by stress when it is applied to the skin surface.

The adhesive sheet 5 bonded to the electrode plate 1 as shown in FIGS. 4 and 5 serves to further improve adhesive properties over the long time when the biomedical electrode is applied to the skin surface and to prevent its falling during measurement of the electrical signal. Currently available medical and surgical adhesive sheets can be used as the adhesive sheet. It is more advisable to use the adhesive sheet having a directional strength perpendicular to the direction to which the conductive tongue 4 rises, to prevent that the electrode plate 1 tears from the edge of cut 3 when the electrically conductive tongue 4 rises.

The adhesive sheet is prepared from a plastic film such as a uniaxially or biaxially stretched film or a woven fabric in which a number of stapled thread or yarns are changed or material thereof is changed.

As described above, the biomedical electrode according to the present invention is designed to form the electrically conductive tongue in the inside region of the electrode plate for connecting to the biomedical diagnostic apparatus by utilizing the cut, so that the electrically conductive tongue is easily connected to the lead wire terminal, when it is attached thereto, by merely rising the tongue through the cut resulting in simplier operation required for the connection as compared with the conventional biomedical electrode having the tab outside thereof. Further, since the electrically conductive adhesive layer does not arise from the surface of the living body after connection, and the weight load after connection to the lead wire terminal is applied to the entire biomedical electrode, poor adhesion due to the local load and instability of the electric signal resulted therefrom can be improved.

As is apparent from the drawings, the biomedical electrode of the present invention has the advantages that since the electrically conductive tongue for connection is disposed in the inside region of the electrode plate through the cut, the expensive material for the electrode plate can be used without loss, the compact package is possible, and the bulk thereof for storage can be reduced.

Since the cut is formed in the non-contact area where the electrically conductive adhesive layer is not substantially adhered to the electrode plate, the electrically conductive tongue can be easily risen through the cut when the tongue is connected to the lead wire terminal. However, in order to connect the tongue to the lead wire terminal more easily, it is preferable to dispose the thick non-tacky member in the non-contact area so that the tongue is automatically made upright by stress when the biomedical electrode is adhered to the skin surface.

While the invention has been described in detail and with reference to specific embodiments thereof, it will be apparent to one skilled in the art that various changes and modifications can be made therein without departing from the spirit and scope thereof.

What is claimed is:

1. A biomedical electrode comprising a flexible electrode plate capable of conforming to a skin surface of a living body, an electrically conductive adhesive layer adhered to a first portion of said electrode plate and to a non-tacky member not adhered to said electrode plate interpositioned between a second portion of said electrode plate and said conductive adhesive layer, wherein the second portion of said electrode plate has a cut therein which provides a tongue adapted to be connected to a terminal of a biomedical diagnostic device.

2. A biomedical electrode as in claim 1, wherein the non-tacky member is selected from the group consisting of plastic films, a woven fabric, a nonwoven fabric, papers and metals.

3. A biomedical electrode as in claim 1, wherein the non-tacky member has a thickness of 0.5 mm. to about 10 mm.

4. A biomedical electrode as in claim 1, wherein said electrode plate comprises a laminate of an electrically conductive layer and an electrically insulating layer, and said electrically conductive adhesive layer is provided on the side of said electrically conductive layer.

5. A biomedical electrode as in claim 4, wherein said electrically insulating layer is a laminate comprising at least two layers.

6. A biomedical electrode as in claim 1, wherein said non-tacky member is an elastomer.

7. A biomedical electrode as in claim 6, wherein said elastomer is a foamed article.

8. A biomedical electrode as in claim 1, wherein an adhesive sheet is applied to said electrode plate on one side thereof so as to extend from the margin thereof.

9. A biomedical electrode as in claim 1, wherein the non-tacky member is embedded in said electrically conductive layer.

* * * * *